United States Patent [19]
O'Leary et al.

[11] Patent Number: 5,290,558
[45] Date of Patent: Mar. 1, 1994

[54] FLOWABLE DEMINERALIZED BONE POWDER COMPOSITION AND ITS USE IN BONE REPAIR

[75] Inventors: Robert K. O'Leary, Spring Lake, N.J.; Patrick A. McBrayer, Yardley, Pa.

[73] Assignee: Osteotech, Inc., Shrewsbury, N.J.

[21] Appl. No.: 573,458

[22] Filed: Aug. 27, 1990

Related U.S. Application Data

[63] Continuation-in-part of Ser. No. 410,596, Sep. 21, 1989, Pat. No. 5,073,373.

[51] Int. Cl.$^5$ ............... A61K 35/32; A61K 47/06; A61K 47.26; A61K 47/36
[52] U.S. Cl. ............................. 424/422; 424/423; 424/549; 623/16; 514/772; 514/777
[58] Field of Search ............ 424/422, 423, 549; 623/16

[56] References Cited

U.S. PATENT DOCUMENTS

| | | | |
|---|---|---|---|
| 3,458,397 | 7/1969 | Myers et al. | 195/2 |
| 4,191,747 | 3/1980 | Scheicher | 424/94.62 |
| 4,430,760 | 2/1984 | Smestad | 3/1.9 |
| 4,440,750 | 4/1984 | Glowacki et al. | 424/95 |
| 4,458,733 | 7/1984 | Lyons | 141/1 |
| 4,563,489 | 1/1986 | Urist | 524/21 |
| 4,595,713 | 6/1986 | St. John | 523/105 |
| 5,053,049 | 10/1991 | Campbell | 623/16 |

FOREIGN PATENT DOCUMENTS

| | | |
|---|---|---|
| 0082621 | 6/1983 | European Pat. Off. . |
| 61-9059 | 3/1986 | Japan . |
| 8607265 | 12/1986 | PCT Int'l Appl. . |
| 8904646 | 6/1989 | PCT Int'l Appl. . |
| 2175807 | 10/1986 | United Kingdom . |

OTHER PUBLICATIONS

Covey et al., "Clinical Induction of Bone Repair With Demineralized Bone Matrix or a Bone Morphogenetic Protein", *Orthopaedic Review*, vol. XVIII, No. 8, pp. 857–863 (Aug. 1989).

Gekko et al., "Mechanism of Protein Stabilization by Glycerol: Preferential Hydration in Glycerol-Water Mixtures", vol. 20, No. 16, pp. 4667–5676 (1981).

Habal et al., "Autologous Corticocancellous Bone Paste for Long Bone Discontinuity Devects: An Experimental Approach", *Annals of Plastic Surgery*, vol. 15, No. 2, pp. 138–142 (Aug., 1985).

McLaughlin et al., "Enhancement of Bone Ingrowth by the use of Bone Matrix as a Biologic Cement", *Clinical Orthopaedics and Related Research*, No. 183, pp. 255 (Mar., 1984).

*Primary Examiner*—Thurman K. Page
*Assistant Examiner*—James M. Spear
*Attorney, Agent, or Firm*—Dilworth & Barrese

[57] ABSTRACT

A flowable demineralized bone powder composition is provided for use in surgical bone repair.

21 Claims, No Drawings

FLOWABLE DEMINERALIZED BONE POWDER COMPOSITION AND ITS USE IN BONE REPAIR

CROSS REFERENCE TO RELATED APPLICATIONS

This application is a continuation-in-part of copending U.S. patent application Ser. No. 07/410,596 filed Sep. 21, 1989, now U.S. Pat. No. 5,073,373.

BACKGROUND OF THE INVENTION

This invention relates to a flowable demineralized bone powder composition and to the use of the composition in the surgical repair of bone defects.

The use of demineralized bone powder in the repair of bone defects has been a subject of investigation for some time. Bone powder contains one or more substances, possibly bone morphogenic protein (BMP), which induce bone regeneration at the defect site. See, e.g., Covey et al., "Clinical Induction of Bone Repair with Demineralized Bone Matrix or a Bone Morphogenetic Protein", *Orthopaedic Review*, Vol XVII, No. 8, pp. 857–863 (August, 1989).

According to Habal et al., "Autologous Corticocancellous Bone Paste for Long Bone Discontinuity Defects: An Experimental Approach", *Annals of Plastic Surgery*, Vol. 15, No. 2, pp. 138–142 (Aug. 1985), autogenous bone which has been granulated into a pastelike material and combined with autogenous blood has been used in the repair of long bone defects in dogs.

SUMMARY OF THE INVENTION

It is an object of the invention to provide a flowable demineralized bone powder composition for use in surgical bone repair.

It is a particular object of the invention to provide a composition of liquid or pastelike consistency comprising demineralized osteogenic bone powder and a liquid polyhydroxy compound as a carrier for the bone powder with or without such optional ingredients as thixotropic agents, medicaments, and the like, and to apply the composition at a bone defect site to induce new bone ingrowth at the site.

In keeping with these and related objects of the invention, there is provided a flowable composition comprising demineralized osteogenic bone powder in a biocompatible carrier, the carrier being selected from a member of the group consisting of liquid polyhydroxy compound, liquid polyhydroxy compound derivative, liquid solution of solid polyhydroxy compound, liquid solution of solid polyhydroxy compound derivative and mixtures thereof.

Application of the foregoing composition to the site of a bone defect, e.g., one resulting from injury, infection, malignancy or developmental malformation, leads to rapid new bone ingrowth by one or more mechanisms such as osteogenesis, osteoconduction and osteoinduction.

The bone powder composition of this invention can be readily prepared when and as needed, preferably with the components of the composition, the means for their combination to provide the composition and the means for applying the composition to a bone defect site being provided in the form of a unitary kit. Alternatively, the bone powder composition can be prepared beforehand and stored in the sterile condition for later use, optionally within the means which will be used to apply the composition to the bone defect site.

DESCRIPTION OF THE PREFERRED EMBODIMENTS

The demineralized pulverized or powdered bone component of the composition herein is a known type of material and is prepared in accordance with known procedures. The expressions "pulverized bone", "powdered bone" and "bone powder" as used herein shall be understood to include bone particles of a wide range of average particle size ranging from relatively fine powders to coarse grains and even larger chips. So, for example, the bone powder present in the composition of this invention can range in average particle size from about 0.1 to about 1.2 cm and preferably from 0.2 to about 1.0 cm. The bone powder can be obtained from about cortical, cancellous and/or corticocancellous autogenous, allogeneic or xenogeneic bone tissue. In general, allogeneic bone tissue is preferred as the source of bone powder.

In a preferred bone demineralization procedure, the bone is first pulverized to the desired average particle size followed by defatting/disinfecting and acid demineralization treatments. A preferred defatting/disinfectant solution is an aqueous solution of ethanol, the ethanol being a good solvent for lipids and the water being a good hydrophilic carrier to enable the solution to penetrate more deeply into the bone. The aqueous ethanol solution also disinfects the bone by killing vegetative microorganisms and viruses. Ordinarily at least about 10% to 40% water (i.e., about 60% to 90% defatting agent such as alcohol) should be present in the defatting, disinfecting solution to produce optimal lipid removal and disinfection within the shortest period of time. The preferred concentration range of the defatting solution is about 60% to 85% alcohol and most preferably 70% alcohol. Following defatting, the bone is immersed in acid over time to effect demineralization. Acids which can be employed in this operation include inorganic acids such as hydrochloric acid and organic acids such as peracetic acid. After acid treatment, the bone powder is rinsed with sterile water for injection, buffered with a buffering agent to a final predetermined pH and then finally rinsed with water for injection to remove residual amounts of acid and buffering agent. The demineralized bone powder can be used immediately for preparation of the composition of this invention or it can be stored under aseptic conditions, advantageously in a freeze-dried state, prior to such preparation.

If desired, the bone powder can be modified in one or more ways, e.g., the porosity of the bone powder can be increased and/or the bone powder can be treated with one or more modifying agents, e.g., glutaraldehyde, as disclosed in U.S. Pat. No. 4,678,470. Another optional treatment involves augmenting or altering the bone protein content of the powdered bone as described in U.S. Pat. Nos. 4,743,259 and 4,902,296.

Any of a variety of medically/surgically useful substances can be incorporated in the flowable bone powder composition herein, e.g., by adding the substance(s) to the bone powder component, e.g., by soaking or immersing the bone particles in a solution or dispersion of the desired substance, by adding the substance(s) to the polyhydroxy compound component or by adding the substances directly to the flowable bone powder composition. Medically/surgically useful substances which can be readily incorporated in the flowable bone powder composition of this invention include, e.g., collagen and insoluble collagen derivatives, hydroxy apatite, etc., and soluble solids and/or liquids dissolved therein, e.g., antiviricides, particularly those effective against HIV and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin and gentamycin, etc.; amino acids, peptides, vitamins, inorganic elements, co-factors for protein synthesis; hormones; endocrine tissue or tissue fragments; synthesizers; enzymes such as collagenase, peptidases, oxidases, etc.; polymer cell scaffolds with parenchymal cells; angiogenic drugs and polymeric carriers containing such drugs; collagen lattices; biocompatible surface active agents; antigenic agents; cytoskeletal agents; cartilage fragments, living cells such as chondrocytes, bone marrow cells, mesenchymal stem cells, natural extracts, tissue transplants, bioadhesives, bone morphogenic proteins (BMPs), transforming growth factor (TGF-beta), insulin-like growth factor (IGF-1); growth hormones such as somatotropin; bone digestors; antitumor agents; fibronectin; cellular attractants and attachment agents; immuno-suppressants; permeation enhancers, e.g., fatty acid esters such as laureate, myristate and stearate monoesters of polyethylene glycol, enamine derivatives, alpha-keto aldehydes, etc.; nucleic acids; and, bioerodable polymers such as those disclosed in U.S. Pat. Nos. 4,764,364 and 4,765,973 and European Patent Application 168,277. The amounts of such optionally added substances can vary widely with optimum levels being readily determined in a specific case by routine experimentation.

To provide the demineralized allogeneic bone powder composition of this invention, the demineralized bone powder is combined with a biocompatible liquid polyhydroxy compound which functions as a carrier or suspension agent for the bone powder.

The expressions "liquid polyhydroxy compound" and "liquid polyhydroxy compound derivative" as employed herein are intended to include those compounds of this type which in the pure or highly concentrated state and at ambient temperature, e.g., 15°-40° C., are flowable liquids. The expressions "solid polyhydroxy compound" and "solid polyhydroxy compound derivative" as employed herein are intended to include those compounds of this type which in the pure or concentrated state and at ambient temperature are normally solid or semi-solid but are soluble in a suitable solvent, e.g., water, physiological saline, ethanol, glycerol, glucose, propylene glycol, polyethylene glycol of from 200-1000 molecular weight, etc., or mixtures thereof, to provide a liquid composition. Functionally, the carrier component of the bone powder composition serves to provide a flowable material of widely varying consistency. The term "flowable" in this context applies to compositions whose consistencies range from those which can be described as shape-sustaining but readily deformable, e.g., those which behave like putty, to those which are runny. Specific forms of flowable bone powder compositions include cakes, pastes, creams and fillers.

Useful polyhydroxy compounds possess from 2 to about 18 carbons and include such classes of compounds as the acyclic polyhydric alcohols, non-reducing sugars, sugar alcohols, sugar acids, monosaccharides, disaccharides, water-soluble or water dispersible oligosaccharides, polysaccharides and known derivatives of the foregoing. Specific polyhydroxy compounds include ethylene glycol, diethylene glycol, triethylene glycol, 1,2-propanediol, trimethylolethane, trimethylopropane, erythritol, pentaerythritol, polyalkylene glycols such as the polyethylene glycols, xylitol, sorbitol, mannitol, dulcitol, arabinose, xylose, ribose, adonitol, arabitol, rhamose, inositol, fructose, galactose, glucose, mannose, sorbose, sucrose, maltose, lactose, maltitol, lactitol, stachyose, maltopentaose, cyclomaltohexaose, carrageenan, agar, alginic acid, guar gum, gum tragacanth, locust bean gum, gum arabic, xanthan gum, amylose, mixtures of any of the foregoing, and the like.

Derivatives of the foregoing polyhydroxy compounds, in particular, ester derivatives thereof, are also useful. For example, liquid and solid monoesters and diesters of glycerol can be used to good effect, the solid esters being dissolved up to the limit of their solubilities in a suitable vehicle, e.g., propylene glycol, glycerol, polyethylene glycol of 200-1000 molecular weight, etc. Liquid glycerol esters include monacetin and diacetin and solid glycerol esters include such fatty acid monoesters of glycerol as glycerol monolaurate which is preferred, glyceryl monopalmitate, glyceryl monostearate, etc. An especially preferred carrier herein comprises glyceryl monolaurate dissolved in glycerol or a 4:1 to 1:4 mixture of glycerol and propylene glycol.

Of the foregoing polyhydroxy compounds, glycerol and its liquid monoesters and diesters, e.g., monacetin and diacetin, fructose, glucose and sucrose, and mixtures thereof are preferred. Where the polyhydroxy compound is a solid, e.g., sucrose, a solvent such as water, glycerol, polyethylene glycol of from 200-1000 average molecular weight, or mixture thereof is used to preferred provide a flowable solution or paste of the compound.

Where, in a particular bone powder composition, the bone powder has a tendency to quickly or prematurely separate from the carrier or to otherwise settle out from the composition such that application of a fairly homogeneous composition is rendered difficult or inconvenient, it can be advantageous to include within the composition a substance whose thixotropic characteristics prevent or reduce this tendency. Thus, e.g., where the carrier component is glycerol and separation of bone powder occurs to an excessive extent where a particular application is concerned, a thickener such as a solution of polyvinyl alcohol, polyvinylpyrrolidone, cellulosic ester such as hydroxypropyl methylcellulose, carboxyl methylcellulose, pectin, food-grade texturizing agent, gelatin, dextran, collagen, starch, hydrolyzed polyacrylonitrile, hydrolyzed polyacrylamide, polyelectrolyte such as polyacrylic acid salt, etc. can be combined with the carrier in an amount sufficient to significantly improve the suspension-keeping characteristics of the composition.

As previously indicated, the bone powder composition of this invention can be freshly prepared just prior to use by mixing of the bone powder, carrier and optional component(s) in any suitable sequence of separate mixing operations or all at once. Thus, the bone powder can be mixed with the optional ingredient(s) and thereafter combined with the carrier component, the bone powder can be mixed with the carrier followed by addition of the optional ingredient(s) or the optional ingredients can be added to the carrier followed by addition of the bone powder. Variations of these sequences of mixing operations are, of course, possible. The amount of bone powder which can be incorporated into the composition of this invention can vary widely with the amounts of from about 5 to about 90 weight percent, and preferably from about 20 to about 80 weight percent, being entirely suitable in most cases, the balance of the composition being made up of carrier. To facilitate on-site preparation of the composition herein, the bone powder, preferably in lyophilized form, and carrier (the latter containing any of the optional ingredients identified above) can be stored in separate packages or containers under sterile conditions and brought together in intimate admixture at the moment of use for immediate application to a bone defect site employing any suitable means, e.g., a syringe, spatula, etc. U.S. Pat. No. 4,458,733, the contents of which are incorporated by reference herein, describes a combined storage mixing and application device which can be adapted to perform the foregoing functions of storage, mixing and application. Alternatively, the bone powder composition can be prepared well in advance and stored under sterile conditions until required for use, e.g., in the barrel of a syringe or other suitable applicator device.

The bone powder composition of this invention can be applied to the bone defect in a variety of ways, e.g., by packing the site with the composition provided in the form of a highly viscous paste. Among the bone repair applications for which the use of the bone powder composition of this invention is eminently suited are: standard or custom arthroplasty prosthesis; reconstruction of skeletal or other osseous defects; enhancing or augmenting the effectiveness of internal and external fixation devices, bone plates, etc.; as a replacement of corticocancellous strips, and so forth.

The following examples are illustrative of the preparation of the flowable demineralized bone powder composition of this invention.

EXAMPLE 1

A quantity of allogeneic cortical or cancellous bone which has been pulverized and sieved to an average particle size of from about 100 to about 500 microns is introduced into a reactor which is then sealed. A 70% ethanol solution at a rate of 30 milliliters per gram of bone is introduced into the reactor followed by agitation for 1 hour (Bolander et al., *Journal of Bone and Joint Surgery*, Vol. 68-A, No. 8 (Oct. 1986)) to effect defatting and disinfecting of the bone powder. Following drainage of the ethanol, a 0.6N solution of HCl at 50 ml per gram of bone is introduced into the reactor (Bolander et al., ibid.), the reaction proceeding for 3 hours (Glowackie, *AATB Workshop*, 11th Annual meeting (1987)). Following drainage of the HCl, the bone is covered and rinsed three times with water for injection (WFI) with the WFI being replaced at 5 minute intervals. Following drainage of the WFI, the bone is completely covered with 0.1M sodium phosphate, a procedure which is repeated until the pH of the solution falls between 6.8 and 7.4. The rinsing procedure with WFI is repeated to provide demineralized cortical or cancellous bone powder ready for mixing with the carrier component to provide the flowable composition of this invention.

The foregoing demineralized bone powder, 25 gm, and injectable grade glycerol, 95 gm, were thoroughly mixed to provide a composition of pastelike consistency. The composition is readily applied to a bone defect site, e.g., employing a syringe, spatula, dental gun or other suitable device.

EXAMPLE 2

The demineralized bone powder of Example 1 was combined with a flowable mixture of 50 weight percent fructose and 50 weight percent dextrose at three different levels to provide flowable demineralized bone powder pastes containing 25, 35 and 50 weight percent bone powder. The bone powder pastes were firm, smooth and of even composition throughout and hardened in air over a period of 8-12 hours.

Similar results can be obtained employing an aqueous sucrose solution as the liquid polyhydroxy compound carrier for the bone powder.

What is claimed is:

1. A flowable composition for application to a bone defect site to promote new bone growth at the site which comprises a new bone growth-inducing amount of demineralized osteogenic bone powder in a biocompatible carrier, the carrier being selected from a member of the group consisting of liquid polyhydroxy compound, liquid polyhydroxy compound ester, liquid solution of solid polyhydroxy compound, liquid solution of solid polyhydroxy compound ester and mixtures thereof, wherein the carrier is on of the following components (i)-(iv);
  (i) the carrier is selected from the group consisting of glycerol, glycerol monoester and glycerol diester;
  (ii) the carrier is selected from the group consisting of monosaccharide, monosaccharide ester, disaccharide, disaccharide ester, oligosaccharide, oligosaccharide ester and mixture thereof;
  (iii) the carrier is a fatty acid monoester dissolved in a solvent which is a different liquid polyhydroxy compound and/or ester thereof; and
  (iv) the carrier is glycerol monolaurate dissolved in a solvent.

2. The composition of claim 1 containing at least one additional ingredient selected from at least one of bone morphogenic protein, transforming growth factor and insulin-like growth factor (IGF-1).

3. The composition of claim 1 wherein the carrier is one of the following components (1) and (2):
  (1) the carrier is selected from the group consisting of fructose, glucose, sucrose and mixtures thereof; and
  (2) the carrier is glycerol monolaurate dissolved in a solvent which is a different liquid polyhydroxy compound and/or ester thereof.

4. A flowable composition for application to a bone defect site to promote new bone growth at the site which consists essentially of a new bone growth-inducing amount of demineralized osteogenic bone powder in a biocompatible carrier, the carrier being selected from a member of the group consisting of liquid polyhydroxy compound, liquid polyhydroxy compound ester, liquid solution of solid polyhydroxy compound, liquid solution of solid polyhydroxy compound ester and mixtures thereof, wherein the polyhydroxy compound is selected from the group consisting of acyclic polyhydric alcohols, non-reducing sugars, sugar alcohols, sugar acids, monosaccharides, disaccharides, water-soluble or water dispersible oligosaccharides, polysaccharides, polyalkylene glycols and mixture thereof.

5. The composition of claim 4 containing at least one additional ingredient selected from the group consisting of antiviral agent, antimicrobial agent, antibiotic agent, amino acid, peptide, vitamin, protein synthesis co-factor, hormone, endocrine tissue, synthesizer, enzyme, polymer-cell scaffolding agent with parenchymal cells, angiogenic drug, polymeric drug carrier, antigenic agent, cytoskeletal agent, mesenchymal stem cells, bone digester, antitumor agent, cellular attractant, fibronectin, growth hormone cellular attachment agent, immunosuppressant, nucleic acid, surface active agent, hydroxy apatite and penetration enhancer.

6. The composition of claim 1 wherein the polyhydroxy compound is selected from the group consisting of ethylene glycol, diethylene glycol, triethylene glycol, 1,2-propanediol, trimethylolethane, trimethylolpropane, erythritol, pentaerythritol, polyethylene glycols, xylitol, sorbitol, mannitol, dulcitol, arabinose, xylose, ribose, adonitol, arabitol, rhamose, inositol, fructose, galactose, glucose, mannose, sorbose, sucrose, maltose, lactose, maltitol, lactitol, stachyose, maltopentaose, cyclomaltohexaose, carrageenan, agar, alginic acid, guar gum, gum tragacanth, locust bean gum, gum arabic, xanthan gum, amylose and mixture thereof.

7. A flowable composition for application to a bone defect site to promote new bone growth at the site which comprises a new bone growth-inducing amount of demineralized osteogenic bone powder in a biocompatible carrier, the carrier being selected from a member of the group consisting of liquid polyhydroxy compound, liquid polyhydroxy compound ester, liquid solution of solid polyhydroxy compound, liquid solution of solid polyhydroxy compound ester and mixtures thereof,
   wherein the carrier is one of the following components (i)–(vi):
   (i) the carrier is a liquid solution of sucrose;
   (ii) the carrier is a liquid solution of a fatty acid monoester of glycerol;
   (iii) the carrier is a fatty acid monoester dissolved in a solvent selected from the group consisting of propylene glycol, glycerol, monoacetin, diacetin, liquid polyethylene glycol and mixtures thereof;
   (iv) the carrier is a flowable solution or paste of sucrose and glycerol;
   (v) the carrier is a flowable solution or paste of sucrose and polyethylene glycol; and
   (vi) the carrier is selected from the group consisting of fructose, dextrose and mixtures thereof.

8. The composition of claim 7 wherein the carrier is one of the following components (1) and (2):
   (1) the carrier is an aqueous solution of sucrose; and
   (2) the carrier is glycerol monolaurate dissolved in a solvent selected from the group consisting of propylene glycol, glycerol, monoacetin, diacetin, liquid polyethylene glycol and mixtures thereof.

9. The composition of claim 8 wherein the carrier is glyceryl monolaurate dissolved in glycerol or a 4:1 to 1:4 mixture of glycerol and propylene glycol.

10. A flowable composition for application to a bone defect site to promote new bone growth at the site which comprises a new bone growth-inducing amount of demineralized osteogenic bone powder in a biocompatible carrier, the carrier being selected from a member of the group consisting of liquid polyhydroxy compound, liquid polyhydroxy compound ester, liquid solution of solid polyhydroxy compound, liquid solution of solid polyhydroxy compound ester and mixtures thereof,
   wherein the polyhydroxy compound is selected from the group consisting of acyclic polyhydric alcohols, non-reducing sugars, sugar alcohols, sugar acids, monosaccharides, disaccharides, water-soluble or water dispersible oligosaccharides, polysaccharides, polyalkylene glycols and mixtures thereof.

11. The composition of claim 10 wherein the polyhydroxy compound is selected from the group consisting of ethylene glycol, diethylene glycol, triethylene glycol, 1,2-propanediol, trimethylolethane, trimethylolpropane, erythritol, pentaerythritol, polyethylene glycols, xylitol, sorbitol, mannitol, dulcitol, arabinose, xylose, ribose, adonitol, arabitol, rhamose, inositol, fructose, galactose, glucose, mannose, sorbose, sucrose, maltose, lactose, maltitol, lactitol, stachyose, maltopentaose, cyclomaltohexaose, carrageenan, agar, alginic acid, guar gum, gum tragacanth, locust bean gum, gum arabic, xanthan gum, amylose and mixtures thereof.

12. The composition of claim 10 wherein said demineralized osteogenic bone powder has been subjected to acid demineralization treatment.

13. The composition of claim 10 wherein the average particle size of the demineralized bone powder is from about 0.1 to about 1.2 cm.

14. The composition of claim 10 wherein the average particle size of the demineralized bone powder is from about 0.2 to about 1 cm.

15. The composition of claim 10 wherein the demineralized bone powder is derived from cortical bone, cancellous and/or corticocancellous autogenous, xenogeneic and/or allogeneic bone tissue.

16. The composition of claim 10 containing from about 5 to about 90 weight percent demineralized bone powder and from about 10 to about 95 weight percent carrier.

17. The composition of claim 10 containing from about 20 to about 80 weight percent demineralized bone powder and from about 20 to about 80 weight percent carrier.

18. The composition of claim 10 containing at least one additional ingredient selected from the group consisting of antiviral agent, antimicrobial agent, antibiotic agent, amino acid, peptide, vitamin, protein synthesis co-factor, hormone, endocrine tissue, synthesizer, enzyme, polymer-cell scaffolding agent with parenchymal cells, angiogenic drug, polymeric drug carrier, collagen lattice, antigenic agent, cytoskeletal agent, mesenchymal stem cells, bone digester, antitumor agent, cellular attractant, fibronectin, growth hormone cellular attachment agent, immunosuppressant, nucleic acid, surface active agent, hydroxy apatite and penetration enhancer.

19. The composition of claim 10 containing a bioerodable polymer.

20. The composition of claim 10 additionally comprising a thickener selected from at least one of polyvinyl alcohol, polyvinylpyrrolidone, hydroxypropyl methylcellulose, carboxyl methylcellulose, pectin, food-grade texturizing agent, gelatin, dextran, collagen, starch, hydrolyzed polyacrylonitrile, hydrolyzed polyacrylamide and polyacrylic acid salt.

21. The composition of claim 12 wherein said demineralized bone powder has additionally been subjected to defatting/disinfecting treatment.

* * * * *